(12) United States Patent
Evans et al.

(10) Patent No.: US 12,102,352 B1
(45) Date of Patent: Oct. 1, 2024

(54) MAGNETIC SUCTIONING SURGICAL CANNULA APPARATUS, SYSTEM AND METHOD

(71) Applicants: Robert Michael Evans, Santa Fe, NM (US); George Crawford, Anniston, AL (US)

(72) Inventors: Robert Michael Evans, Santa Fe, NM (US); George Crawford, Anniston, AL (US)

(*) Notice: Subject to any disclaimer, the term of this patent is extended or adjusted under 35 U.S.C. 154(b) by 0 days.

(21) Appl. No.: 18/597,603

(22) Filed: Mar. 6, 2024

(51) Int. Cl.
| | |
|---|---|
| A61B 17/02 | (2006.01) |
| A61B 17/34 | (2006.01) |
| A61M 1/00 | (2006.01) |
| A61B 17/00 | (2006.01) |

(52) U.S. Cl.
CPC .......... *A61B 17/3421* (2013.01); *A61B 17/02* (2013.01); *A61M 1/80* (2021.05); *A61B 2017/00836* (2013.01); *A61B 2017/00876* (2013.01); *A61B 2217/005* (2013.01); *A61B 2218/008* (2013.01)

(58) Field of Classification Search
CPC .......... A61B 17/3421; A61B 17/02; A61B 2017/00836; A61B 2017/00876; A61B 2217/005; A61B 2218/008; A61M 1/80
USPC ................................ 600/205, 210, 213, 227
See application file for complete search history.

(56) References Cited

U.S. PATENT DOCUMENTS

| | | | | |
|---|---|---|---|---|
| 4,642,128 | A * | 2/1987 | Solorzano | A61B 18/00 55/467 |
| 5,336,169 | A * | 8/1994 | Divilio | A61B 18/00 604/319 |
| 9,610,130 | B2 | 4/2017 | Vayser et al. | |
| 9,999,345 | B2 | 6/2018 | Vayser et al. | |
| 11,622,756 | B2 | 4/2023 | Swift | |
| 2014/0155701 | A1* | 6/2014 | Jayaraj | A61B 90/30 606/49 |
| 2014/0323811 | A1 | 10/2014 | DeSantis et al. | |
| 2016/0008088 | A1* | 1/2016 | Vayser | A61B 90/57 600/249 |
| 2017/0035404 | A1 | 2/2017 | Foster et al. | |
| 2017/0281255 | A1* | 10/2017 | Babini | B01D 46/0041 |
| 2019/0159830 | A1* | 5/2019 | Horner | A61B 18/1402 |
| 2022/0054720 | A1* | 2/2022 | Hajarian | A61M 1/86 |
| 2023/0126084 | A1* | 4/2023 | Blackhurst | G08B 21/182 604/24 |
| 2023/0310057 | A1* | 10/2023 | Kirschman | A61B 18/082 606/28 |

* cited by examiner

*Primary Examiner* — Eduardo C Robert
*Assistant Examiner* — David C Comstock
(74) *Attorney, Agent, or Firm* — The Law Firm of Andrea Hence Evans, LLC

(57) ABSTRACT

A Magnetic Suctioning Cannula Apparatus (MSCA) for evacuating smoke during surgical procedures. The Magnetic Suctioning Cannula Apparatus (MSCA) may enhance a surgeon's visibility and provide a safer environment by minimizing exposure to hazardous particles during surgical procedures. The Magnetic Suctioning Cannula Apparatus (MSCA) may provide a connection process through a built-in magnetic housing component whereby the magnetic housing component attaches to a surgical retractor.

8 Claims, 12 Drawing Sheets

MAGNETIC SUCTIONING SURGICAL CANNULA APPARATUS, SYSTEM AND METHOD

FIELD OF INVENTION

Embodiments disclosed herein relate to a magnetic suctioning cannula apparatus, more particularly to a magnetic suctioning cannula apparatus for use with a surgical instrument, a retractor, and suction management system.

BACKGROUND OF THE INVENTION

In many surgical procedures, the utilization of various instruments, such as cannulas, retractors, and suction systems, serves distinct functions in addressing specific challenges and achieving surgical objectives. Cannulas, for instance, may be used to find application in diverse scenarios, ranging from the establishment of intravenous access for the administration of fluids and medications, to their role in arthroscopic procedures, enabling the introduction of an arthroscope into joints for diagnostic or surgical purposes. Additionally, in cardiac surgeries, cannulas may be instrumental in implementing cardiopulmonary bypass, effectively diverting blood away from the heart during procedures like open-heart surgery.

In a broad range of surgical procedures, retractors may play a pivotal role in providing surgeons with enhanced visibility and access to the surgical site. For example, in abdominal surgeries, retractors may be employed to delicately hold back abdominal walls and organs, facilitating procedures such as laparotomy. In other instances, neurosurgeons may utilize retractors to gently manipulate brain tissue, allowing them to access specific regions of the brain during intricate procedures. In other instances, such as orthopedic surgeries, retractors may aid in exposing bones and joints, crucial for interventions like joint replacement surgery.

In many surgical procedures, suction systems, are indispensable for maintaining a clear surgical field by removing blood, fluids, and debris. General surgical procedures commonly may benefit from suction systems to ensure an unobstructed view. For example, in plastic and reconstructive surgeries, suction may be utilized to remove excess fat during procedures like liposuction, contributing to refined aesthetic outcomes. In another surgical example, suction systems may play a critical role in clearing the chest cavity for thoracic surgeries, enhancing the precision of the surgical process.

Despite the versatility and efficacy of these tools, there are still damaging aspects of these surgical procedures. For example, surgical procedures may generate smoke and debris, particularly when using electrocautery or laser devices. This surgical smoke poses challenges, impairing visibility and potentially exposing the surgical team to harmful byproducts. It would be more desirable to facilitate smoke evacuation procedures and tools to promote a safer surgical site and operating field. Thus, there is a need for a secure and stable structure configured to be a smoke evacuation cannula for surgical procedures.

Improved smoke evacuation cannulas are essential due to the persistent challenges posed by surgical smoke, a byproduct which may be generated during procedures involving electrocautery and other energy-based devices. This specialized tool addresses the need for enhanced visibility during surgery, as surgical smoke can obscure the operative field, potentially leading to errors and compromised precision. Moreover, the health and safety of the surgical team are at stake, as inhalation of the smoke may contain harmful particles, posing respiratory risks. In many instances, regulatory compliance, patient safety, and overall procedure efficiency are also driving factors, emphasizing the importance of providing for advanced smoke evacuation means.

Accordingly, there remains a need for improved smoke evacuation cannula structures for surgical procedures. This need and other needs are satisfied by the various aspects of the present disclosure.

SUMMARY OF THE INVENTION

In accordance with the principles of the present invention, a Magnetic Suctioning Cannula Apparatus (MSCA) is provided. The Magnetic Suctioning Cannula Apparatus (MSCA) may be configured to efficiently capture and remove surgical smoke during surgical procedures, ensuring a clearer operative field. A Magnetic Suctioning Cannula Apparatus (MSCA) may be provided whereby the apparatus may enhance a surgeon's view during surgical procedures. In one or more instances, a Magnetic Suctioning Cannula Apparatus (MSCA) may be provided whereby the apparatus is configured to contribute to a safer environment for the surgical team by minimizing their exposure to potentially hazardous particles.

In one or more instances, incorporating a Magnetic Suctioning Cannula Apparatus (MSCA) may provide for a higher standard of safety for both patients and medical professionals in surgical procedures and surgical environments. The Magnetic Suctioning Cannula Apparatus (MSCA) may provide an improved crucial advancement in optimizing procedural outcomes for surgical procedures. Magnetic Suctioning Cannula Apparatus (MSCA) is configured to provide technological advancements and improved ergonomic design.

The Magnetic Suctioning Cannula Apparatus (MSCA) provides an innovative solution configured for seamless integration with various stainless steel retractors providing versatility across a wide array of open surgical procedures in diverse medical disciplines. In one aspect, this Magnetic Suctioning Cannula Apparatus (MSCA) effortlessly adheres to retractors through a built-in magnetic housing component, thereby streamlining the connection process between retractors and the Magnetic Suctioning Cannula Apparatus (MSCA).

The Magnetic Suctioning Cannula Apparatus (MSCA) may be operatively connected in a systematic manner, having a connection on one end to a suction management system. The suction management system maybe be a standard suction system including but not limited to an operating room wall suction or a mobile system. In as least one aspect, the Magnetic Suctioning Cannula Apparatus (MSCA) efficiently addresses the issue of hazardous surgical smoke generated during open surgeries.

In some aspects, the Magnetic Suctioning Cannula Apparatus (MSCA) safeguards surgical teams and patients from potential health risks linked to surgical smoke exposure. In other aspects, the Magnetic Suctioning Cannula Apparatus (MSCA) sets a new benchmark for safety and procedural efficiency in the medical domain. This Magnetic Suctioning Cannula Apparatus (MSCA) provides a safer and more efficient surgical environment.

Additional aspects of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several aspects of the invention and together with the description, serve to explain the principles of the invention.

Figure 1:
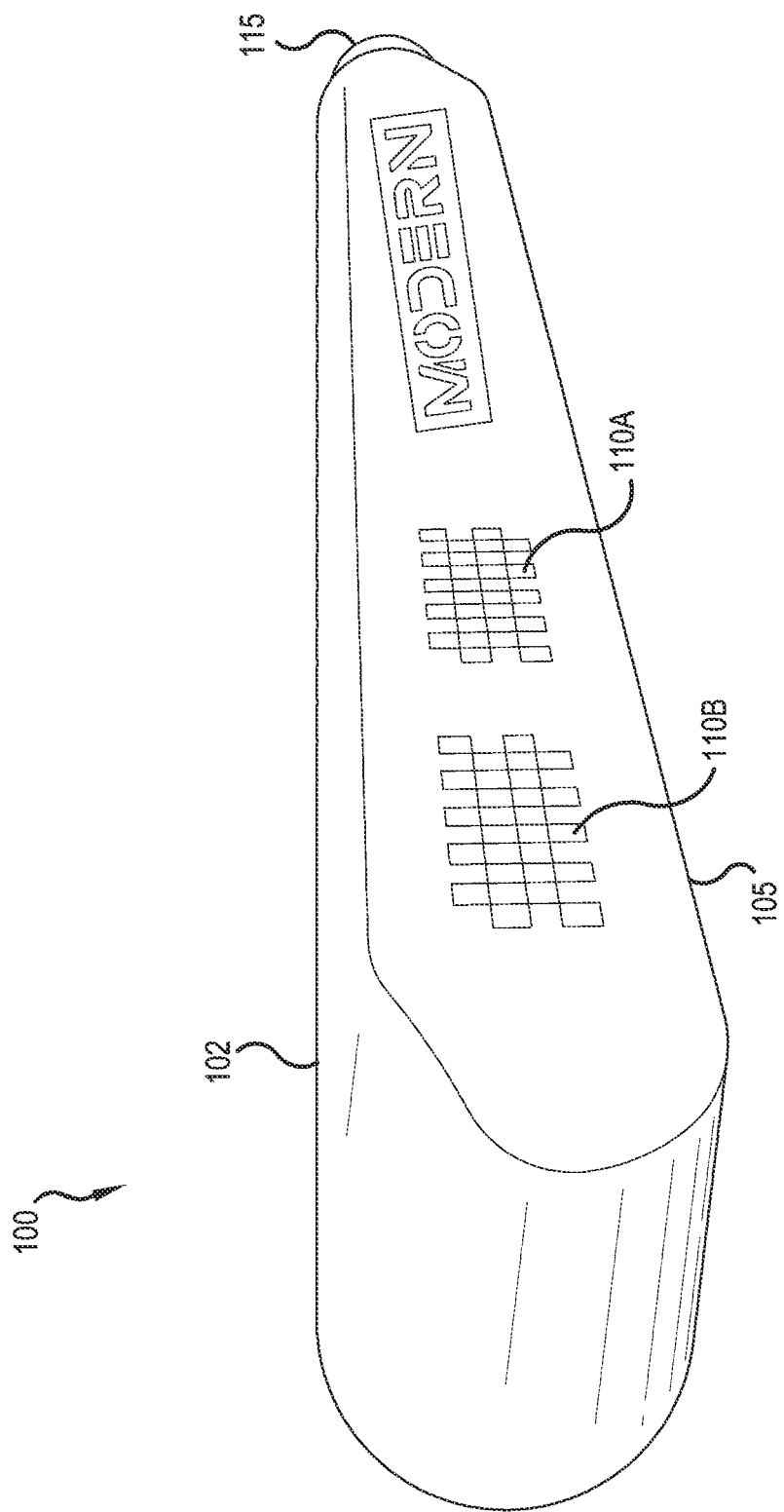
FIG. 1 shows a perspective view of the Magnetic Suctioning Cannula Apparatus (MSCA), in accordance with an exemplary embodiment of the present invention.

Reference is made in the following detailed description to accompanying drawings, which form a part hereof, wherein like numerals may designate like parts throughout that are corresponding and/or analogous. It will be appreciated that the figures have not necessarily been drawn to scale, such as for simplicity and/or clarity of illustration. For example, dimensions of some aspects may be exaggerated relative to others. Further, it is to be understood that other embodiments may be utilized. Furthermore, structural and/or other changes may be made without departing from claimed subject matter. References throughout this specification to "claimed subject matter" refer to subject matter intended to be covered by one or more claims, or any portion thereof, and are not necessarily intended to refer to a complete claim set, to a particular combination of claim sets (e.g., method claims, apparatus claims, etc.), or to a particular claim. It should also be noted that directions and/or references, for example, such as up, down, top, bottom, and so on, may be used to facilitate discussion of drawings and are not intended to restrict application of claimed subject matter. Therefore, the following detailed description is not to be taken to limit claimed subject matter and/or equivalents.

DETAILED DESCRIPTION OF THE INVENTION

The present invention can be understood more readily by reference to the following detailed description of the invention and the Examples included therein.

Before the present articles, systems, devices, and/or methods are disclosed and described, it is to be understood that they are not limited to specific manufacturing methods unless otherwise specified, or to particular materials unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited.

Definitions

It is also to be understood that the terminology used herein is for the purpose of describing particular aspects only and is not intended to be limiting. As used in the specification and in the claims, the term "comprising" can include the aspects "consisting of" and "consisting essentially of." Unless defined otherwise, all technical and scientific terms used herein have the same meaning as commonly understood by one of ordinary skill in the art to which this invention belongs. In this specification and in the claims which follow, reference will be made to a number of terms which shall be defined herein.

As used in the specification and the appended claims, the singular forms "a," "an" and "the" include plural referents unless the context clearly dictates otherwise. Thus, for example, reference to "an opening" can include two or more openings.

Ranges can be expressed herein as from one particular value, and/or to another particular value. When such a range is expressed, another aspect includes from the one particular value and/or to the other particular value. Similarly, when values are expressed as approximations, by use of the antecedent 'about,' it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

The terms "first," "second," "first part," "second part," and the like, where used herein, do not denote any order, quantity, or importance, and are used to distinguish one element from another, unless specifically stated otherwise.

As used herein, the terms "optional" or "optionally" means that the subsequently described event or circumstance can or cannot occur, and that the description includes instances where said event or circumstance occurs and instances where it does not. For example, the phrase "optionally affixed to the surface" means that it can or cannot be fixed to a surface.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

Disclosed are the components to be used to manufacture the disclosed devices, systems, and articles of the invention as well as the devices themselves to be used within the methods disclosed herein. These and other materials are disclosed herein, and it is understood that when combinations, subsets, interactions, groups, etc. of these materials are disclosed that while specific reference of each various individual and collective combinations and permutation of these materials cannot be explicitly disclosed, each is specifically contemplated and described herein. For example, if a particular material is disclosed and discussed and a number of modifications that can be made to the materials are discussed, specifically contemplated is each and every combination and permutation of the material and the modifications that are possible unless specifically indicated to the contrary. Thus, if a class of materials A, B, and C are disclosed as well as a class of materials D, E, and F and an example of a combination material, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the articles and devices of the invention. Thus, if there are a variety of additional steps that can be performed it is understood that each of these additional steps can be performed with any specific aspect or combination of aspects of the methods of the invention.

It is understood that the devices and systems disclosed herein have certain functions. Disclosed herein are certain structural requirements for performing the disclosed functions, and it is understood that there are a variety of structures that can perform the same function that are related to the disclosed structures, and that these structures will typically achieve the same result.

As briefly described above, the present disclosure relates, in various aspects, to a Magnetic Suctioning Cannula Apparatus (MSCA). In one aspect, the present disclosure provides a Magnetic Suctioning Cannula Apparatus (MSCA) its system and associated devices. The Magnetic Suctioning Cannula Apparatus (MSCA) is needed to address the problem of surgical smoke exposure during open surgeries. In one or more instances, surgical teams are vulnerable to inhaling toxic particles and gases, posing serious health risks. This Magnetic Suctioning Cannula Apparatus (MSCA) provides a proactive solution, mitigating these risks and establishing a safer operating environment for everyone involved. In one or more instances, the Magnetic Suctioning Cannula Apparatus (MSCA) may be referred to by a commercial brand name uniquely associated with the Magnetic Suctioning Cannula Apparatus (MSCA).

In further aspects, the Magnetic Suctioning Cannula Apparatus (MSCA) comprises one or more of the following:

A. A housing, wherein the housing comprises a smoke evacuation system, a magnetic housing component, and a cannula. Wherein the housing is operatively connected to a suction management system. In one or more embodiments, the housing may be a substantially contoured obround shape;

B. An electrosurgical device, wherein the electrosurgical device comprises a generator and a handpiece with one or more electrodes. In one or more instances, the electrosurgical device may be controlled by a switch on the handpiece or other component. In one or more instances, the electrosurgical device produces a variety of electrical waveforms which interact with tissues for surgical procedures. In one or more embodiments, electrosurgical devices are integral to various surgical specialties, utilizing high-frequency electrical currents for tissue manipulation. For example, in some instances electrosurgical pencils and handheld instruments are common tools used in surgical procedures for precise cutting and coagulation. In one or more instances, electrosurgical devices may facilitate controlled incisions while concurrently cauterizing blood vessels, reducing bleeding during surgery. In other aspects, electrocautery units, can employ different handpieces based on surgical needs including incorporating cutting and coagulation functions. In one or more instances, surgical lasers, such as $CO_2$ lasers, cut or vaporize tissue causing smoke to be emitted during surgical procedures. The electrosurgical device may be paired with a Magnetic Suctioning Cannula Apparatus (MSCA) whereby, the emitted smoke may be efficiently captured and suctioned away from the operating field. In all instances, the suction system and suction tube element remain independent of and not directly connected to the electrosurgical device.

C. A magnetic housing component, wherein the magnetic housing component may be built-in into the housing of the Magnetic Suctioning Cannula Apparatus (MSCA). The magnetic housing component is configured to be operatively couples to surgical retractors, whether handheld or self-retaining, at any position;

D. A smoke evacuation system, wherein the smoke evacuation system in operatively coupled to at least one of a suction system via a suction tube element, and a venting element. The smoke evacuation system suction tube element further comprises a flexible silicone distal end with the venting element further comprising lateral and distal suction vents configured to offer highly efficient smoke removal from the surgical field.

In one aspect, the Magnetic Suctioning Cannula Apparatus (MSCA) boasts an ergonomic design, enabling easy maneuverability and precise placement to ensure effective smoke evacuation without disrupting surgical procedures. In another aspect, the Magnetic Suctioning Cannula Apparatus (MSCA) provides an integrated solution which may be seamlessly integrated with standard surgical instruments in a modular or bonded piece. The Magnetic Suctioning Cannula Apparatus (MSCA) thereby eliminates the need for additional equipment, minimizing workflow disruptions. In another aspect, the Magnetic Suctioning Cannula Apparatus (MSCA) provides enhanced safety for patients, surgeons, and medical staff by diverting surgical smoke away from the patient, surgeon and the surgical team. In another aspect, the Magnetic Suctioning Cannula Apparatus (MSCA) further minimizes the risk of respiratory issues, eye irritation, and long-term health hazards associated with exposure to harmful toxins.

In a further aspect, the Magnetic Suctioning Cannula Apparatus (MSCA) may be operatively coupled to medical devices including but not limited to electrosurgical devices, bipolar electrosurgical instruments featuring two active electrodes, and other surgical devices configured to surgically impact localized tissue effects. In other aspects, the Magnetic Suctioning Cannula Apparatus (MSCA) may be particularly useful in delicate procedures requiring precise coagulation. In further aspects, the Magnetic Suctioning Cannula Apparatus (MSCA) may be utilized in conjunction with electrosurgical devices including LigaSure® devices which use radiofrequency energy and pressure to seal blood vessels, minimizing bleeding and enhancing the surgical field. In one or more aspects, the Magnetic Suctioning Cannula Apparatus (MSCA) may be utilized in conjunction with electrosurgical devices including Bovie® devices such as Bovie® Electrosurgical Pencils. In other aspects, the Magnetic Suctioning Cannula Apparatus (MSCA) may be used in conjunction with ultrasonic scalpels which are configured to utilize high-frequency vibrations for cutting and coagulation. In one or more instances, when utilized with any of the aforementioned or comparable electrosurgical devices, the Magnetic Suctioning Cannula Apparatus (MSCA) provides the benefit of efficient smoke evacuation to manage the smoke generated during the cutting process. In all instances, the suction system and suction tube element remain independent of and not directly connected to the electrosurgical device.

In other aspects, the Magnetic Suctioning Cannula Apparatus (MSCA) may be used in conjunction with radiofrequency ablation devices, whereby radiofrequency ablation devices apply radiofrequency energy to ablate or remove tissue. In some aspects, the Magnetic Suctioning Cannula Apparatus (MSCA) may be used with surgical devices for minimally invasive procedures. In other aspects, the Magnetic Suctioning Cannula Apparatus (MSCA) may be vital to efficiently remove smoke and particulate matter produced during the ablation process. In summary, these electrosurgical devices, when coupled with the Magnetic Suctioning Cannula Apparatus (MSCA), provide for a safer and clearer surgical environment, mitigating potential health risks and improving overall procedural outcomes.

In various aspects, the Magnetic Suctioning Cannula Apparatus (MSCA) may be configured for use with various types of retractors during surgical procedures. In some cases, the Magnetic Suctioning Cannula Apparatus (MSCA) may be utilized with hand-held surgical retractors. In many instances, hand-held retractors are often single pieces like hook-like retractors configured such that the retractors lack a locking mechanism and require manual positioning. In most instances, surgeons are required to either hold these retractors themselves or pass them to an assistant from the medical staff. Commonly used handheld retractors include Senn, Army-Navy, Ribbon (Malleable), Hohmann, Farabeuf, Meyerding, Deaver, and Richardson. Additional handheld retractors, such as Lahey, Blair (Rollet), Ragnell, Linde-Ragnell, Davis, Volkman, Farabeuf, Jackson, Tracheal Hook, Love Nerve, Goelet, and Cushing Vein Retractor, offer further options for surgical professionals.

In some cases, the Magnetic Suctioning Cannula Apparatus (MSCA) may be utilized with self-retaining retractors. In many instances, self-retaining retractors may be regarded as extensions of a surgeon's hands in critical procedures. In most cases, self-retaining retractors are specially designed retracting instruments configured with a unique ratchet system or adjustable lock mechanism, enabling surgeons to open the retractor and secure it in place. Notably, these retractors possess an extensive structure and often incorporate sharp tips or prongs for efficient retraction of incisions and organs. Among the most commonly used self-retaining retractors are the Beckman Retractor, Balfour Retractor, Alms Retractor, Lone Star Retractor, Gelpi Retractor, Gutow Retractor, Weitlaner Retractor, Beckman-Weitlaner Retractor, Beckman-Eaton Retractor, Bookwalter Retractor, and Omni Retractor, offering a diverse array of options for surgical professionals. In surgical settings, retractors play a crucial role in holding tissues aside, providing surgeons with improved visibility and access to the operative site. In many instances, various types of retractors may be used in conjunction with the Magnetic Suctioning Cannula Apparatus (MSCA) to manage the challenges associated with surgical smoke.

In some general cases, surgical procedures may be performed utilizing handheld retractors, such as the Richardson or Deaver retractors, which allow for the gentle retraction of tissues in abdominal surgeries. These retractors can be effectively used with smoke evacuation cannulas to maintain a clear field of vision, minimizing the impact of surgical smoke. In a neurosurgery example, where precision is paramount, specialized retractors like the Greenberg or Yasargil are employed to delicately move brain tissues aside. The integration of a smoke evacuation cannula in these procedures helps ensure optimal visibility by effectively removing surgical smoke generated during electrocautery or laser use. For orthopedic surgeries, including joint replacement procedures, often involve the use of self-retaining retractors like the Gelpi or Weitlaner. These retractors can be complemented by the Magnetic Suctioning Cannula Apparatus (MSCA) to address challenges related to smoke and debris, particularly when using energy-based devices for tissue manipulation.

In plastic and reconstructive surgery, where meticulous tissue handling is essential, specialized retractors like the Joseph or Balfour are employed. When combined with the Magnetic Suctioning Cannula Apparatus (MSCA), these retractors contribute to a clearer operative field by efficiently evacuating smoke generated during procedures like liposuction or tissue sculpting. Thoracic surgeries utilize rib spreaders and thoracotomy retractors, such as the Bookwalter or Finochietto, to access the chest cavity. The incorporation of an Magnetic Suctioning Cannula Apparatus (MSCA) in these procedures is crucial to maintaining visibility by capturing and removing surgical smoke.

Overall, the integration of the Magnetic Suctioning Cannula Apparatus (MSCA) with various types of retractors is essential in modern surgical practices. It addresses the challenges posed by surgical smoke, ensuring optimal visibility for surgeons, minimizing health risks for the surgical team, and contributing to a safer and more efficient surgical environment.

In one or more embodiments the Magnetic Suctioning Cannula Apparatus (MSCA) may be assembled as a modular apparatus or singularly bonded apparatus. In one embodiment, the Magnetic Suctioning Cannula Apparatus (MSCA) may be configured in a first configuration, as a single-use option, presented as a single bonded piece. In this embodiment, users may simply open a sterile package, and the Magnetic Suctioning Cannula Apparatus (MSCA) comes pre-connected, comprising the Magnetic Suctioning Cannula Apparatus (MSCA) tubing, the Magnetic Suctioning Cannula Apparatus (MSCA) comprising lateral vented slots, and a magnetic housing component positioned on the anterior side of the Magnetic Suctioning Cannula Apparatus (MSCA).

In one embodiment, the Magnetic Suctioning Cannula Apparatus (MSCA) may be configured in second configuration presented as a two or more piece modular option. In this embodiment, the Magnetic Suctioning Cannula Apparatus (MSCA) may be configured for assembly within the surgical field as a modular two-piece configuration. In one or more embodiments, this two-piece configuration comprises smoke evacuation tubing and the Magnetic Suctioning Cannula Apparatus (MSCA) being assembled together during the surgical procedure, offering flexibility and adaptability based on the surgical team's preferences and requirements. The Magnetic Suctioning Cannula Apparatus may be configured to offer flexibility in material choices, presenting options between rigid plastic, flexible silicone, and polyurethane, and other surgical grade chemical polymers. In one or more embodiments, the Magnetic Suctioning Cannula Apparatus (MSCA) comprises the use of a flexible material for enhanced adaptability.

In one aspect, the Magnetic Suctioning Cannula Apparatus (MSCA) comprises vented slots at the distal end and both sides laterally. In one or more embodiments, these vented slots may be part of the Magnetic Suctioning Cannula Apparatus (MSCA) housing or part of the smoke evacuation system contained in the Magnetic Suctioning Cannula Apparatus (MSCA) housing. In one or more embodiments, the Magnetic Suctioning Cannula Apparatus (MSCA) may be attached to one or more stainless steel retractors. The stainless steel retractors may be attached to the Magnetic Suctioning Cannula Apparatus (MSCA) by one or more magnets positioned inside the Magnetic Suctioning Cannula Apparatus (MSCA) anteriorly. In one or more embodiments, the magnets may be positioned inside the housing of the Magnetic Suctioning Cannula Apparatus (MSCA) directly or as part of a magnetic housing component.

Still in further aspects, the Magnetic Suctioning Cannula Apparatus (MSCA) provides a design comprising a subtle contour on the anterior surface of the Magnetic Suctioning Cannula Apparatus (MSCA) for optimized functionality. In yet another aspect, the magnets within the Magnetic Suctioning Cannula Apparatus (MSCA) may be strategic placed along the Magnetic Suctioning Cannula Apparatus (MSCA) housing. In one or more embodiments, one or more magnetic elements maybe positioned in various placements within or without the Magnetic Suctioning Cannula Apparatus (MSCA) housing. For example, the Magnetic Suctioning Cannula Apparatus (MSCA) may comprise at least one magnetic element positioned at one or more: internal placements, external placements positioned outside the Magnetic Suctioning Cannula Apparatus (MSCA) housing in direct contact with retractors), or a magnetic additive element added to a Suctioning Cannula Apparatus (SCA) to form a Magnetic Suctioning Cannula Apparatus (MSCA). In one or more instances, the magnetic configuration may provide versatility to cater to diverse surgical preferences and requirements.

Figure 2:
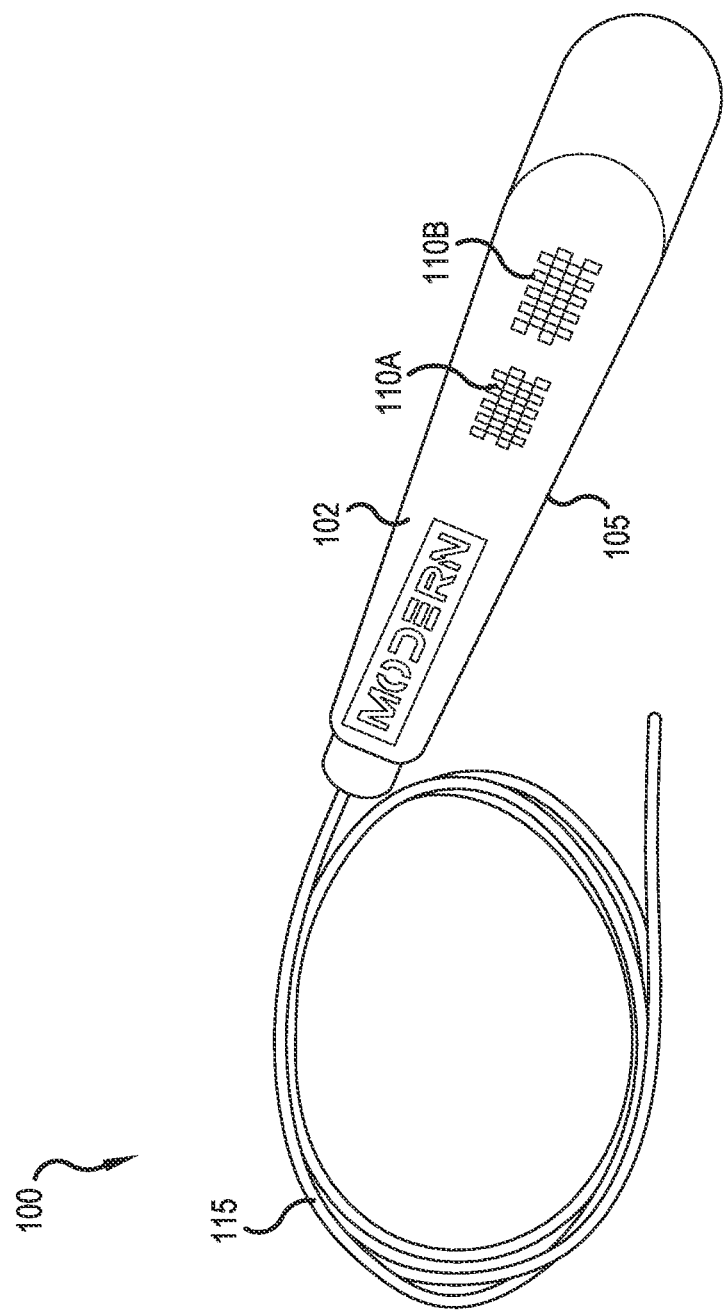
FIG. 2 shows a perspective view of the Magnetic Suctioning Cannula Apparatus (MSCA), in accordance with an exemplary embodiment of the present invention.

FIGS. 1-4, 5A, 5B, 6A, 6B, 7A, 7B, 7C, 9A and 9B best show Magnetic Suctioning Cannula Apparatus (MSCA) 100 connected to a suction management system 310. FIG. 1 shows a perspective view of the Magnetic Suctioning Cannula Apparatus (MSCA), in accordance with an exemplary embodiment of the present invention. Referring again to FIG. 1, the Magnetic Suctioning Cannula Apparatus (MSCA) 100 having a Magnetic Suctioning Cannula Apparatus (MSCA) 100 substantially contoured housing 102. A suction tubing 115 is connected to a first end of the Magnetic Suctioning Cannula Apparatus (MSCA) 100 substantially contoured housing 102 of one or more floor panels 104. A second end of the Magnetic Suctioning Cannula Apparatus (MSCA) 100 substantially contoured housing 102 being closed. In one or more embodiments, the Magnetic Suctioning Cannula Apparatus (MSCA) 100 substantially contoured housing 102 having one or more vented slots 110 on the lateral side of the substantially contoured housing 102. The Magnetic Suctioning Cannula Apparatus (MSCA) 100 substantially contoured housing 102 having a magnetic housing component 105 at the anterior of the Magnetic Suctioning Cannula Apparatus (MSCA) 100 substantially contoured housing 102. FIG. 2 shows another perspective view of the Magnetic Suctioning Cannula Apparatus (MSCA) 100, in accordance with an exemplary embodiment of the present invention.

Figure 3:
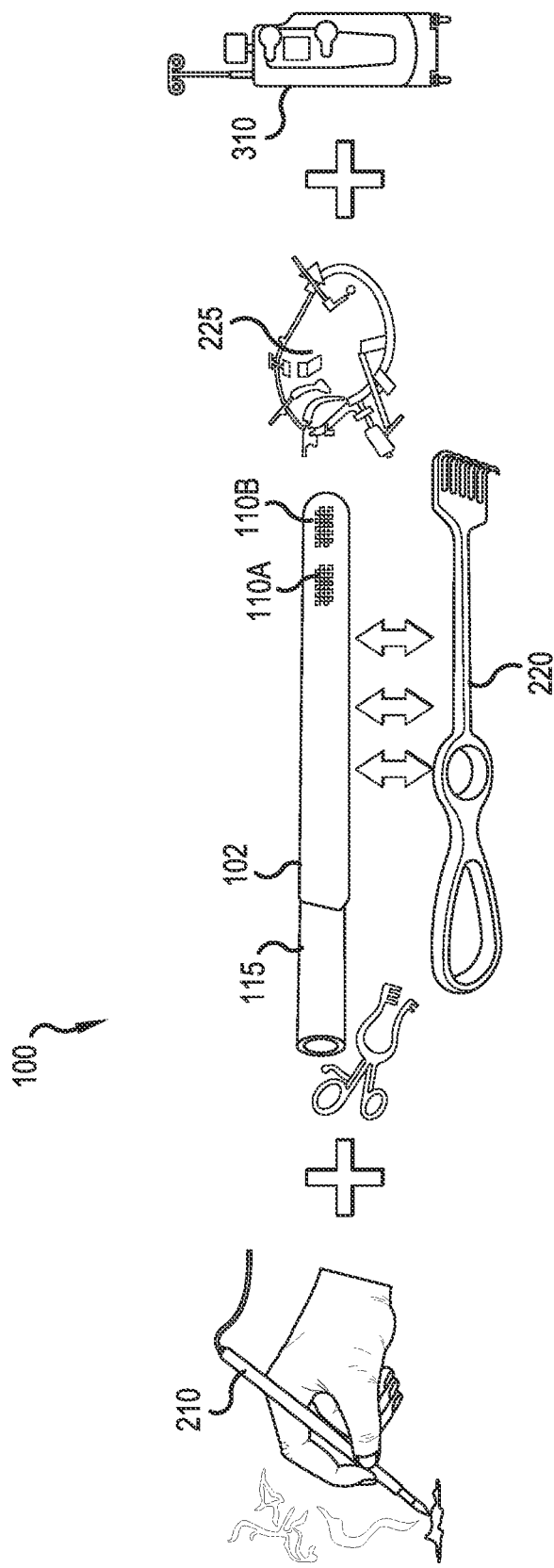
FIG. 3 shows a side view of the Magnetic Suctioning Cannula Apparatus (MSCA) connected to a suction management system, in accordance with an exemplary embodiment of the present invention.

FIG. 3 shows a view of the Magnetic Suctioning Cannula Apparatus (MSCA) 100 connected to a suction management system 310, in accordance with an exemplary embodiment of the present invention. FIG. 3 shows at least one retractor 220 attached to the Magnetic Suctioning Cannula Apparatus (MSCA) 100 substantially contoured housing 102 magnetic housing component 105 at the anterior. FIG. 3 shows the suction tubing 115 attached to the Magnetic Suctioning Cannula Apparatus (MSCA) 100 substantially contoured housing 102. FIG. 3 also shows self retaining retractors 225 that may be attached to the Magnetic Suctioning Cannula Apparatus (MSCA) 100 substantially contoured housing 102 magnetic housing component 105 at the anterior. Furthermore, FIG. 3 shows the Magnetic Suctioning Cannula Apparatus (MSCA) 100 substantially contoured housing 102 magnetic housing component 105 attached to a suction management system 310.

Figure 4A:
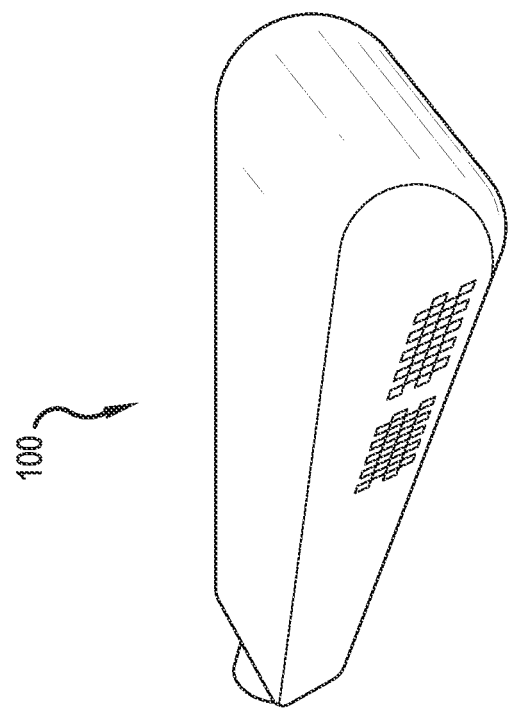
FIG. 4A shows a perspective view of a modular embodiment of the Magnetic Suctioning Cannula Apparatus (MSCA), in accordance with an exemplary embodiment of the present invention.
Figure 4A:
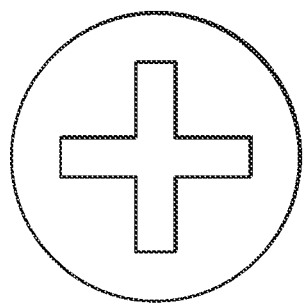
Figure 4A:
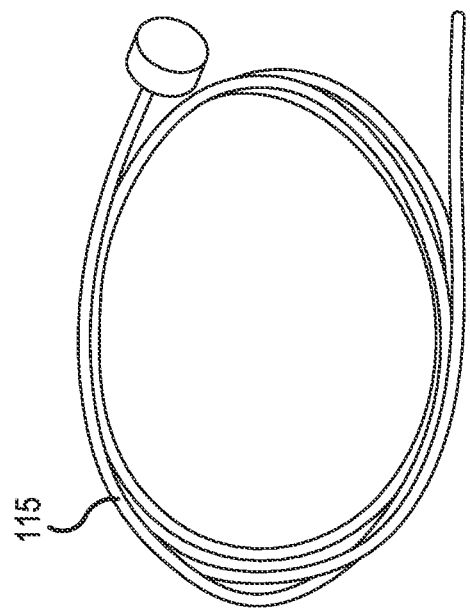
Figure 4B:
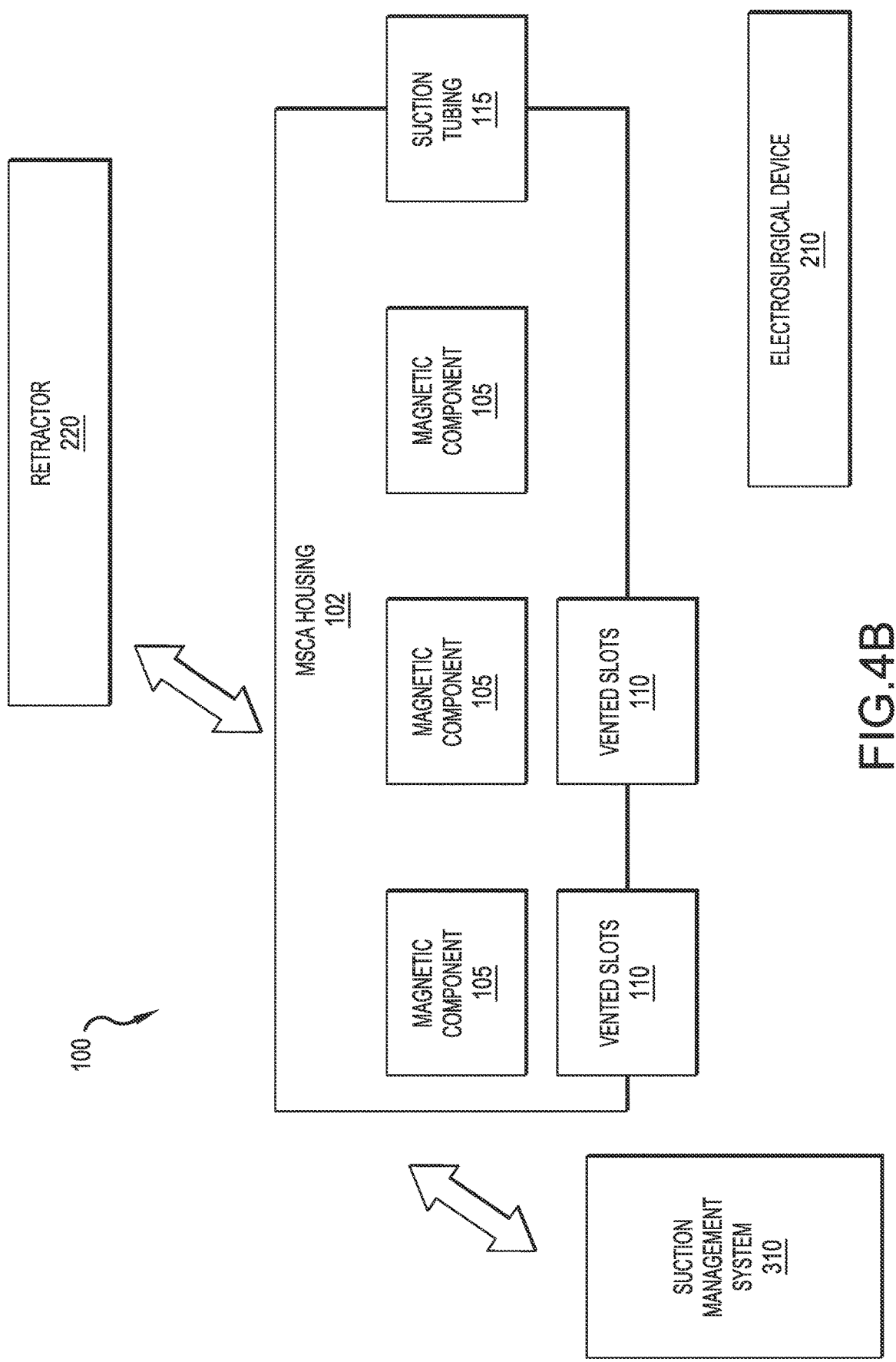
FIG. 4B shows a component view of a modular embodiment of a Magnetic Suctioning Cannula Apparatus (MSCA), in accordance with an exemplary embodiment of the present invention.

FIG. 4A shows a perspective view of a modular embodiment of the Magnetic Suctioning Cannula Apparatus (MSCA) 100 and suction tubing 115, in accordance with an exemplary embodiment of the present invention. FIG. 4B shows a component view of a modular embodiment of a Magnetic Suctioning Cannula Apparatus (MSCA) 100, in accordance with an exemplary embodiment of the present invention. FIG. 4B shows a view of the Magnetic Suctioning Cannula Apparatus (MSCA) 100 connected a suction management system 310, in accordance with an exemplary embodiment of the present invention. FIG. 4B shows at least one retractor 220 attached to the Magnetic Suctioning Cannula Apparatus (MSCA) 100 substantially contoured housing 102 magnetic housing component 105 at the anterior. FIG. 4B shows the suction tubing 115 attached to the Magnetic Suctioning Cannula Apparatus (MSCA) 100 substantially contoured housing 102. FIG. 4B also shows self-retaining retractors 225 that may be attached to the Magnetic Suctioning Cannula Apparatus (MSCA) 100 substantially contoured housing 102 magnetic housing component 105 at the anterior. Furthermore, FIG. 4B shows the Magnetic Suctioning Cannula Apparatus (MSCA) 100 substantially contoured housing 102 magnetic housing component 105 attached to a suction management system 310.

Figure 5A:
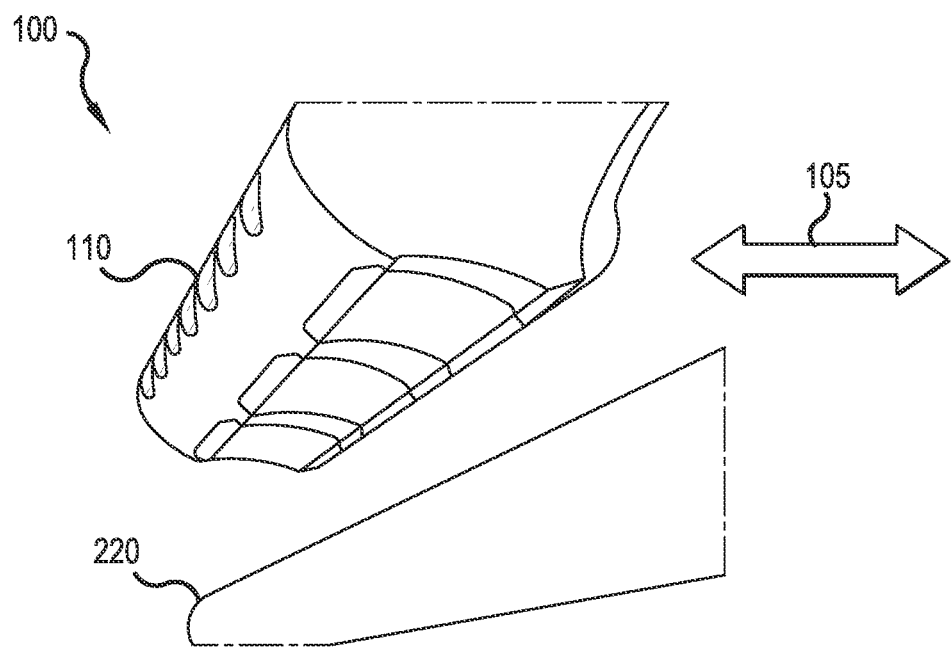
FIG. 5A and FIG. 5B show side plan views of the Magnetic Suctioning Cannula Apparatus (MSCA), in accordance with an exemplary embodiment of the present invention.
Figure 5B:
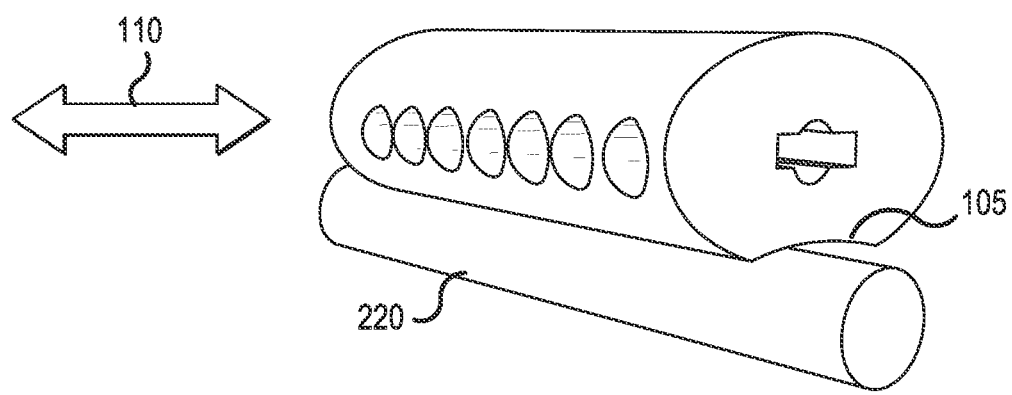

FIG. 5A and FIG. 5B show side plan views of the Magnetic Suctioning Cannula Apparatus (MSCA), in accordance with an exemplary embodiment of the present invention. Referring now to FIGS. 5A and 5B, Magnetic Suctioning Cannula Apparatus (MSCA) 100 comprises vented slots 110 at the distal end and both sides laterally. In one or more embodiments, these vented slots 110 may be part of the Magnetic Suctioning Cannula Apparatus (MSCA) 100 substantially contoured housing 102 or part of a smoke evacuation system contained in the Magnetic Suctioning Cannula Apparatus (MSCA) 100 housing. In one or more embodiments, the Magnetic Suctioning Cannula Apparatus (MSCA) 100 may be attached to one or more stainless steel retractors 220. The stainless steel retractors 220 may be attached to the Magnetic Suctioning Cannula Apparatus (MSCA) 100 by a magnetic housing component 105 comprising one or more magnets positioned inside the Magnetic Suctioning Cannula Apparatus (MSCA) 100 anteriorly. In one or more embodiments, the one or more magnets positioned of the Magnetic Suctioning Cannula Apparatus (MSCA) 100 may be positioned inside the substantially contoured housing 102 of the Magnetic Suctioning Cannula Apparatus (MSCA) 100 directly or as part of an external magnetic housing component 105.

Still in further aspects, the Magnetic Suctioning Cannula Apparatus (MSCA) 100 provides a design comprising a subtle contour on the anterior surface of the Magnetic Suctioning Cannula Apparatus (MSCA) 100 for optimized functionality. In yet another aspect, the magnets within the Magnetic Suctioning Cannula Apparatus (MSCA) may be strategically placed along the Magnetic Suctioning Cannula Apparatus (MSCA) 100 substantially contoured housing 102. In one or more embodiments, one or more magnetic elements maybe positioned in various placements within or without the Magnetic Suctioning Cannula Apparatus (MSCA) 100 substantially contoured housing 102. For example, the Magnetic Suctioning Cannula Apparatus (MSCA) 100 may comprise at least one magnetic element positioned at one or more: internal placements, external placements positioned outside the Magnetic Suctioning Cannula Apparatus (MSCA) 100 substantially contoured housing 102 in direct contact with retractors, or a magnetic additive element added to a Suctioning Cannula Apparatus (SCA) to form a Magnetic Suctioning Cannula Apparatus (MSCA) 100. In one or more instances, the magnetic configuration may provide versatility to cater to diverse surgical preferences and requirements.

Figure 6A:
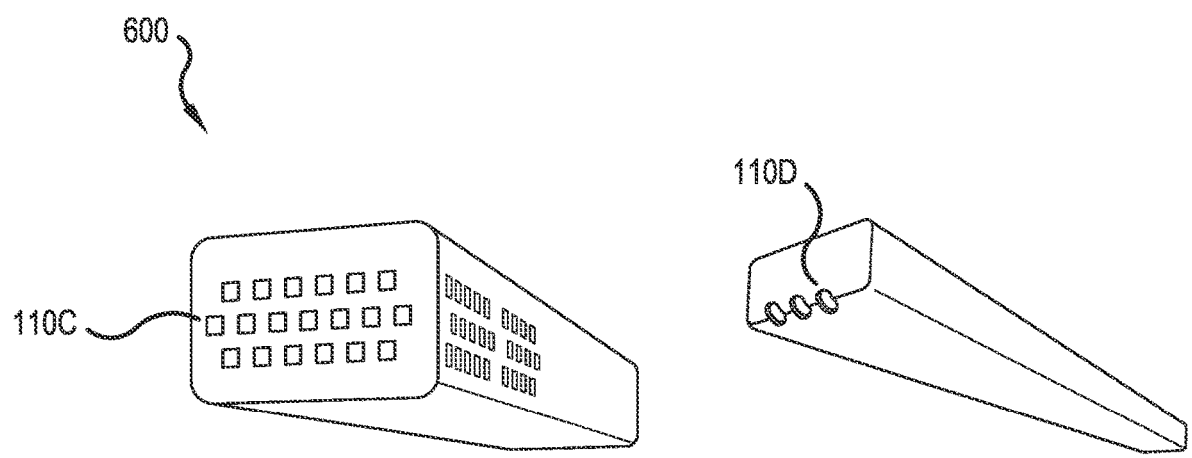
FIGS. 6A and 6B show side plan views of the Magnetic Suctioning Cannula Apparatus (MSCA), in accordance with an exemplary embodiment of the present invention.
Figure 6B:
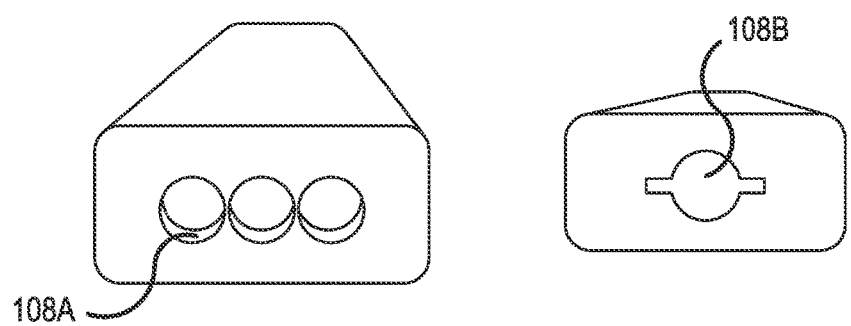

FIGS. 6A and 6B show side plan views of the Magnetic Suctioning Cannula Apparatus (MSCA) 100, in accordance with an exemplary embodiment of the present invention. Referring to FIG. 6A, a smoke evacuation system 600 of the Magnetic Suctioning Cannula Apparatus (MSCA) 100 is depicted. In one or more embodiments, wherein the smoke evacuation system 600 comprises a venting element wherein the venting element further comprises a vented slot 110C, 110D having distal and/or lateral positions on the Magnetic Suctioning Cannula Apparatus (MSCA) 100. Referring to FIG. 6B, the Magnetic Suctioning Cannula Apparatus (MSCA) 100 comprises suction ports 108A and 108B located on distal and lateral positions wherein the suction ports 108A and 108B are configured to operatively connect to a suction management system 310. The smoke evacuation system 600 comprising suction ports 108A and 108B and vented slots 110C and 110D may be housed in a flexible silicone substantially contoured housing 102 the Magnetic Suctioning Cannula Apparatus (MSCA) 100 at lateral and distal positions. The Magnetic Suctioning Cannula Apparatus (MSCA) 100 is configured to offer highly efficient smoke removal from the surgical field.

Figure 7A:
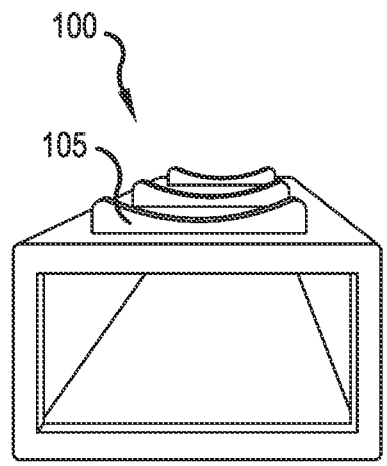
FIGS. 7A, 7B, and 7C shows a side view, perspective view, and a bottom view of the Magnetic Suctioning Cannula Apparatus (MSCA), in accordance with an exemplary embodiment of the present invention.
Figure 7B:
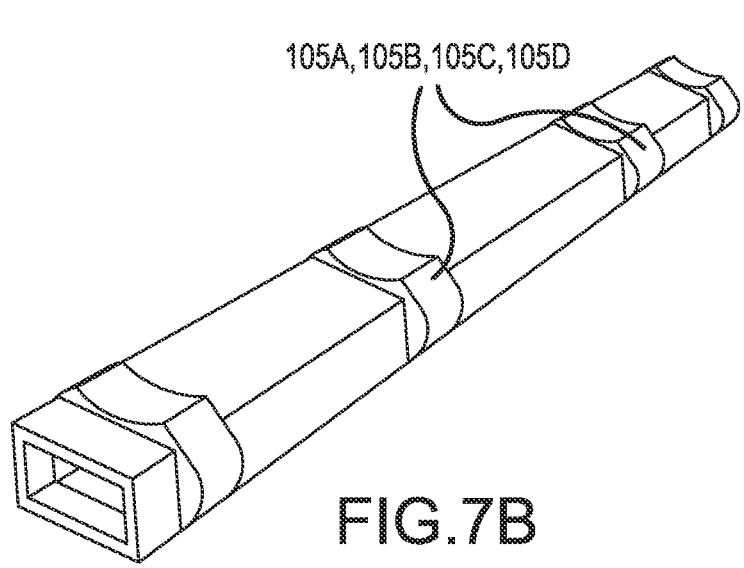
Figure 7C:
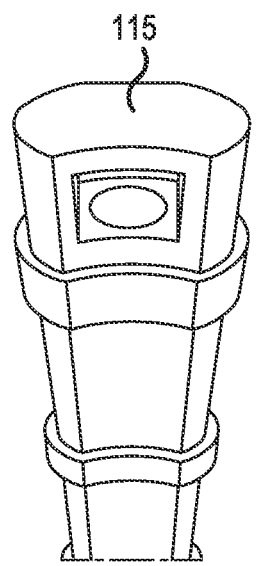

FIGS. 7A, 7B, and 7C shows a side view, perspective view, and a bottom view of the Magnetic Suctioning Cannula Apparatus (MSCA) 100, in accordance with an exemplary embodiment of the present invention. Referring to FIG. 7A, a side view of the Magnetic Suctioning Cannula Apparatus (MSCA) 100 having magnetic housing components 105 place externally on the housing 102 of the Magnetic Suctioning Cannula Apparatus (MSCA) 100 is depicted. Referring to FIG. 7B, a perspective view of the Magnetic Suctioning Cannula Apparatus (MSCA) 100 having magnetic housing components 105 place externally on the housing 102 of the Magnetic Suctioning Cannula Apparatus (MSCA) 100 at positions 105A, 105B, 105C, and 105D is depicted. Referring to FIG. 7C, a bottom anterior view of the Magnetic Suctioning Cannula Apparatus (MSCA) 100 having magnetic housing components 105 place externally on the housing 102 of the Magnetic Suctioning Cannula Apparatus (MSCA) 100 is depicted wherein a suction port 115 is shown at the closed distal end of the Magnetic Suctioning Cannula Apparatus (MSCA) 100.

Figure 9A:
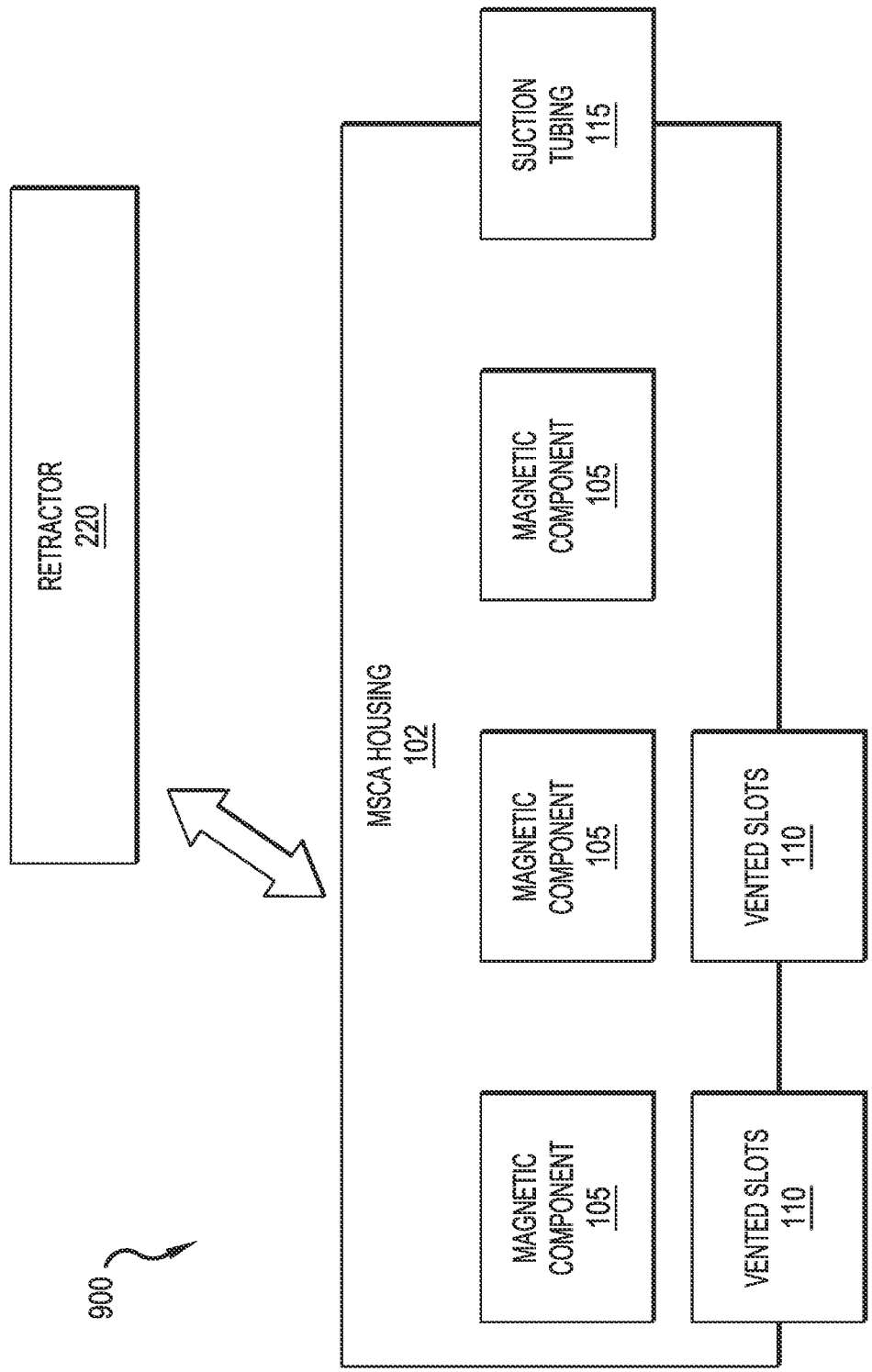
FIGS. 9A and 9B shows a component view of a first configuration of a Magnetic Suctioning Cannula Apparatus (MSCA), in accordance with an exemplary embodiment of the present invention.
Figure 9B:
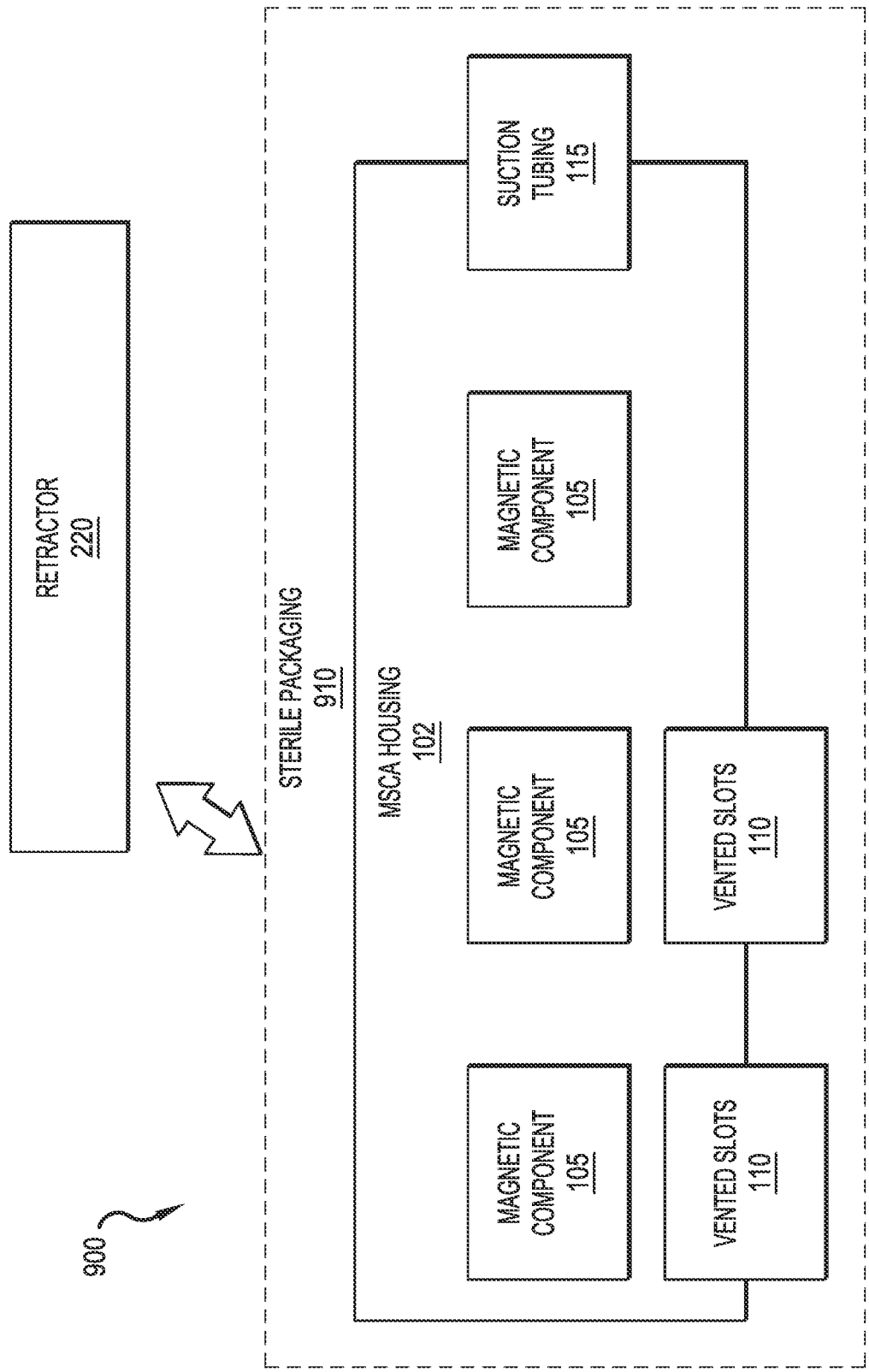

FIGS. 9A and 9B shows a component view of a first configuration of a Magnetic Suctioning Cannula Apparatus (MSCA) 100, in accordance with an exemplary embodiment of the present invention. Referring to FIG. 9A, in at least one embodiment, the Magnetic Suctioning Cannula Apparatus (MSCA) 100 may be configured in a first configuration, as a single-use option, presented as a single bonded piece 900. In this embodiment, users may simply open a sterile package 910 (depicted in FIG. 9B), and the Magnetic Suctioning Cannula Apparatus (MSCA) 100 comes pre-connected, comprising the Magnetic Suctioning Cannula Apparatus (MSCA) housing 102 having suction tubing 115, the lateral or distal vented slots 110, and a magnetic housing component 105 positioned on the anterior side of the Magnetic Suctioning Cannula Apparatus (MSCA).

The present disclosure, according to further aspects, also provides methods of using the disclosed devices and systems. In one aspect, disclosed herein is a method for utilizing a Magnetic Suctioning Cannula Apparatus (MSCA) 100 as depicted in FIGS. 1-4, 5A, 5B, 6A, 6B, 7A, 7B, 7C, 9A and 9B. In further aspects, the disclosed Magnetic Suctioning Cannula Apparatus (MSCA) 100 devices and systems can be used for safe and efficient smoke removal from the surgical field. According to various further aspects of the invention, the efficient smoke removal from the surgical field devices and systems can comprise multiple configurations. For example, various exemplary embodiments of the inventive Magnetic Suctioning Cannula Apparatus (MSCA) 100 devices and systems are shown in FIGS. 1-4, 5A, 5B, 6A, 6B, 7A, 7B, 7C, 9A and 9B.

Figure 8A:
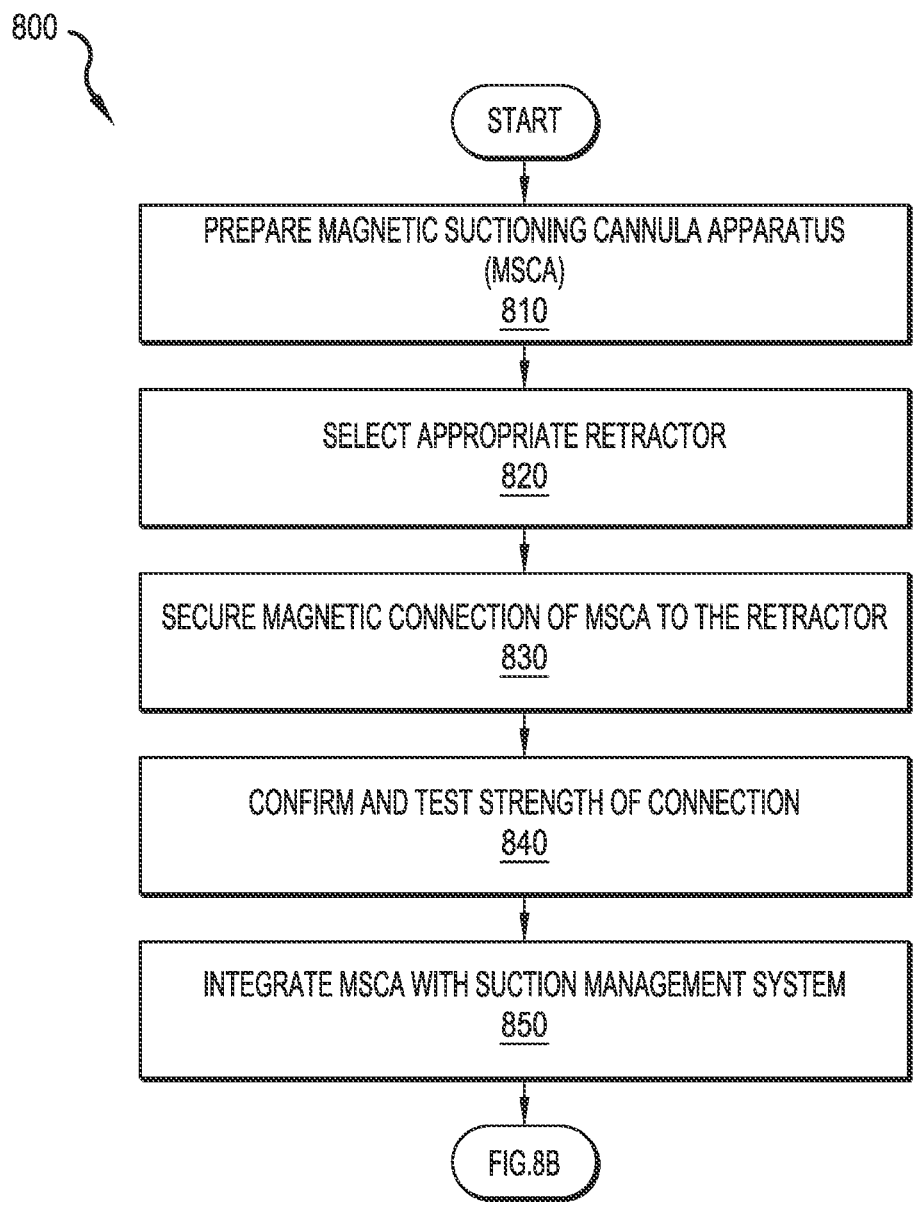
FIGS. 8A and 8B shows a method of using a Magnetic Suctioning Cannula Apparatus (MSCA), in accordance with an exemplary embodiment of the present invention.
Figure 8B:
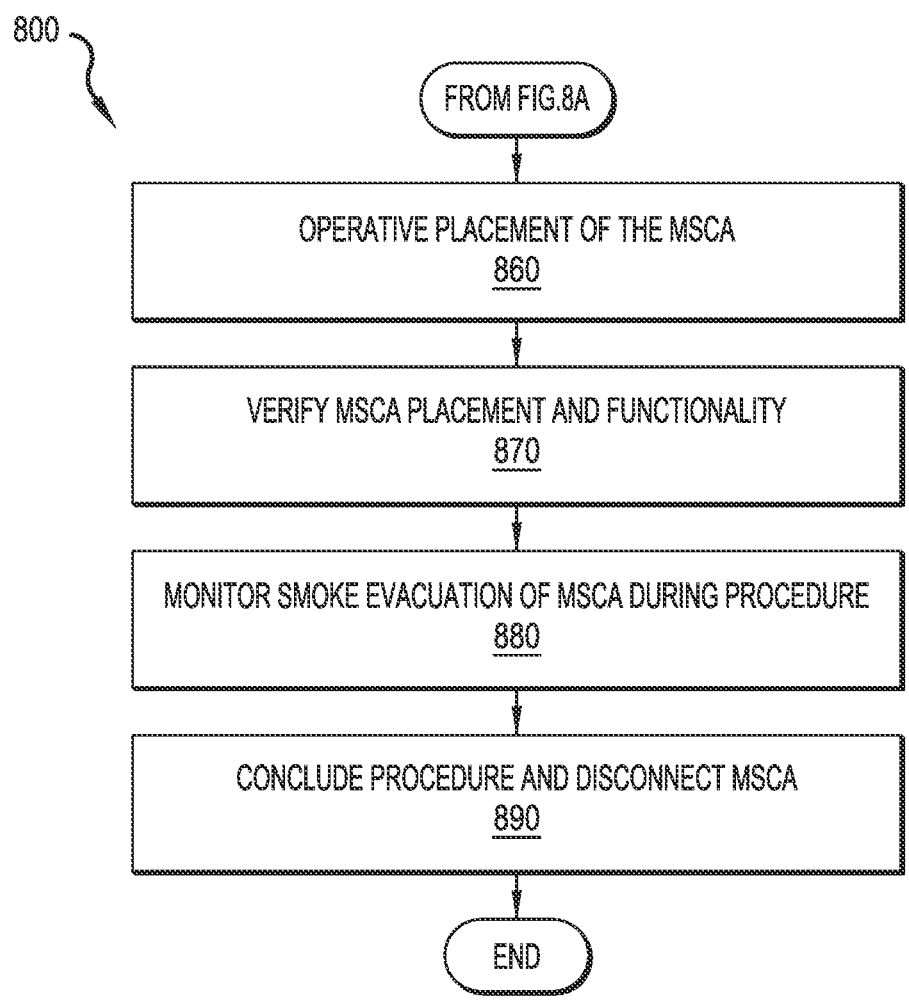

FIGS. 8A and 8B are flow charts setting forth the general stages involved in a method 800 consistent with an embodiment of the disclosure for providing a Magnetic Suctioning Cannula System (MSCS). Method 800 may be implemented using a Magnetic Suctioning Cannula Apparatus (MSCA) 100 as described in more detail below with respect to FIGS. 1-4, 5A, 5B, 6A, 6B, 7A, 7B, 7C, 9A and 9B. FIG. 8 shows a method of using a Magnetic Suctioning Cannula Apparatus (MSCA), in accordance with an exemplary embodiment of the present invention.

Although the stages illustrated by the flow charts are disclosed in a particular order, it should be understood that the order is disclosed for illustrative purposes only. Stages may be combined, separated, reordered, and various intermediary stages may exist. Accordingly, it should be understood that the various stages illustrated within the flow chart may be, in various embodiments, performed in arrangements that differ from the ones illustrated. Moreover, various stages may be added or removed from the flow charts without altering or deterring from the fundamental scope of the depicted methods and systems disclosed herein. Ways to implement the stages of method 800 will be described in greater detail below.

Method 800 may begin at starting block and proceed to stage 810 where Magnetic Suctioning Cannula Apparatus (MSCA) 100 may be prepared for use. For example, a user may begin by ensuring the sterility and integrity of the Magnetic Suctioning Cannula Apparatus (MSCA) 100 upon opening its sterile package. Additionally, a user may inspect the Magnetic Suctioning Cannula Apparatus (MSCA) 100 for any damage or defects.

From stage 810, where Magnetic Suctioning Cannula Apparatus (MSCA) 100 is prepared for use, method 800 may advance to stage 820 where a user may select the suitable stainless steel retractor 220 based on surgical requirements. For example, a user may select a hand-held retractor or self-retaining retractor based on the surgical needs and compatibility with the Magnetic Suctioning Cannula Apparatus (MSCA) 100.

Method 800 may continue to stage 830 where Magnetic Suctioning Cannula Apparatus (MSCA) 100 may be securely magnetically attached to the retractor 220. For example, the Magnetic Suctioning Cannula Apparatus (MSCA) 100 may be magnetically placed on the chosen retractor, utilizing the built-in magnetic housing component 105 for secure attachment. For the strongest connection, a user may ensure that the magnets are oriented properly, either internally or externally on the Magnetic Suctioning Cannula Apparatus (MSCA) 100, based on the intended surgical use.

After Magnetic Suctioning Cannula Apparatus (MSCA) 100 is magnetically attached to the retractor 220 in stage 830, method 800 may proceed to stage 840 where magnetic attachment of the Magnetic Suctioning Cannula Apparatus (MSCA) 100 to the retractor 220 may be confirmed and tested to ensure that it will not move out of place or position. For example, the Magnetic Suctioning Cannula Apparatus (MSCA) 100 securely attached to the retractor 220, providing stability throughout the surgical procedure. The magnetic connection should also allow for easy intentional repositioning, if necessary, which being strong and secure enough to prevent unintentional movement.

Once Magnetic Suctioning Cannula Apparatus (MSCA) 100 is confirmed to be securely magnetically positioned to the retractor 220 in stage 840, method 800 may proceed to stage 850 where Magnetic Suctioning Cannula Apparatus (MSCA) 100 may be integrated with suction management system 310. For example, the Magnetic Suctioning Cannula Apparatus (MSCA) 100 may be connected at one end via a standard suction tubing 115 to a designated suction management system 310. This connection aids in the efficient evacuation of surgical smoke generated during the surgical procedures. Additionally, the Magnetic Suctioning Cannula Apparatus (MSCA) 100 may be connected via the standard suction tubing 115 to the dedicated suction management system 310 to efficiently evacuate surgical smoke.

From stage 850, where Magnetic Suctioning Cannula Apparatus (MSCA) 100 is integrated with suction management system 310, method 800 may advance to stage 860 where the Magnetic Suctioning Cannula Apparatus (MSCA) 100 is operatively placed in the surgical filed. For example, operative placement of the Magnetic Suctioning Cannula Apparatus (MSCA) 100 in the surgical field, ensures that the vented slots 110, located at the distal end and laterally on the MSCA 100, are strategically placed to capture smoke at its source. For specifically, the MSCA 100 should not interfere with the surgeon's movements or compromise the surgical procedure.

Method 800 may continue to stage 870 where the Magnetic Suctioning Cannula Apparatus (MSCA) 100 placement and functionality is confirmed and verified to ensure that it will not move out of place or position. For example, the Magnetic Suctioning Cannula Apparatus (MSCA) 100 must be in a proper placement throughout the surgery, making any necessary adjustments to the position to optimize smoke evacuation. A few tests should be conducted to confirm that the suction management system 310 is functioning effectively to remove surgical smoke.

Once Magnetic Suctioning Cannula Apparatus (MSCA) 100 is confirmed to be securely positioned and operating effectively in stage 870, method 800 may then continue to stage 880 where the Magnetic Suctioning Cannula Apparatus (MSCA) 100 is monitored for efficacy of the smoke evacuation system 600 during the surgical procedure. For example, the Magnetic Suctioning Cannula Apparatus (MSCA) 100 must be continuously monitored throughout the surgical procedure to ensure the medical team's safety by minimizing their exposure to hazardous particles and smoke. In this way, the MSCA 100 contributes to creating a safer and more efficient surgical environment.

Once smoke evacuation system 600 of the Magnetic Suctioning Cannula Apparatus (MSCA) 100 is confirmed to be operating effectively in stage 880, method 800 may then proceed to stage 890 where the surgical procedure is completed and the Magnetic Suctioning Cannula Apparatus (MSCA) 100 is disconnected. Once Magnetic Suctioning Cannula Apparatus (MSCA) 100 is disconnected in stage 895, method 800 may then end.

Method 800 shows the proposed method of use for the Magnetic Suctioning Cannula Apparatus (MSCA) 100 evacuating surgical smoke through a unique "hands-free" approach to suctioning smoke away from the surgical field, offering a single-use solution applicable across various surgical disciplines. In one or more instances, the Magnetic Suctioning Cannula Apparatus (MSCA) 100 comprises rigid plastic, flexible silicone vented slots 110 positioned laterally and/or at the distal end, a magnetic housing component 105 housing magnets, positioned at various points along the anterior surface positioned internally, externally, or incorporated as a magnetic powder additive during manufacturing.

In one or more instances, the Magnetic Suctioning Cannula Apparatus (MSCA) 100 may be adaptable for use with standard suction tubing 115 including but not limited to pre-bonded tubing requiring no assembly. In one or more embodiments, the Magnetic Suctioning Cannula Apparatus (MSCA) 100 may be configured to function as a combined Yankauer suction tip, other standard suction tubing assembly within the surgical field. In one or more instances, the Magnetic Suctioning Cannula Apparatus (MSCA) 100 may be specifically designed for reusable stainless steel surgical retractors 220, encompassing both handheld and self-retaining types. In one or more embodiments, the Magnetic Suctioning Cannula Apparatus (MSCA) 100 may be configured to allow magnets to securely adhere to the retractor surfaces 220.

In one or more instances, the Magnetic Suctioning Cannula Apparatus (MSCA) 100 is not constrained by a particular shape, size, or location of the vented slots 110, either laterally or distally on the surface of the MSCA 100. In one or more instances, the Magnetic Suctioning Cannula Apparatus (MSCA) 100 comprises magnets wherein the placement and quantity of magnets are flexible and can be tailored to specific needs such that the MSCA 100 comprises one or magnets positioned at any location on or within the MSCA 100.

In one or more instances, the Magnetic Suctioning Cannula Apparatus (MSCA) 100 may be implemented in accordance with best practices and standards associated with surgical medical procedures and regulated by authorized regulating authorities. In one or more instances, the Magnetic Suctioning Cannula Apparatus (MSCA) 100 may be configure to perform standard and improved methods for evacuating surgical smoke away from the surgical field, utilizing either wall suction within the surgical room or a mobile waste management system.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way appreciably intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications can be referenced. The disclosures of these publications in their entirety are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein can be different from the actual publication dates, which can require independent confirmation.

The patentable scope of the invention is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

While the specification includes examples, the disclosure's scope is indicated by the following claims. Furthermore, while the specification has been described in language specific to structural features and/or methodological acts, the claims are not limited to the features or acts described above. Rather, the specific features and acts described above are disclosed as examples for embodiments of the disclosure.

Insofar as the description above and the accompanying drawing disclose any additional subject matter that is not within the scope of the claims below, the disclosures are not dedicated to the public and the right to file one or more applications to claims such additional disclosures is reserved.

Although very narrow claims are presented herein, it should be recognized the scope of this disclosure is much broader than presented by the claims. It is intended that broader claims will be submitted in an application that claims the benefit of priority from this application.

What is claimed:

1. A magnetic suctioning cannula apparatus, comprising:
   a housing;
   a magnetic housing component, the magnetic housing component configured to attract one or more surgical tools to at least one surface of the housing;
   a cannula, the cannula having suction tubing operatively connected to an opposing end of the housing;
   a smoke evacuation unit, at least a portion of the smoke evacuation unit connected to at least one of a first side wall and a second side wall;
   wherein the cannula has suction tubing operatively connected to the opposing end of the housing via a suction aperture;
   wherein the magnetic housing component is securely connected to a surgical retractor; and
   wherein the magnetic suctioning cannula apparatus is operatively connected to a suction management system.

2. The magnetic suctioning cannula apparatus of claim 1, wherein the smoke evacuation unit has at least one opening.

3. The magnetic suctioning cannula apparatus of claim 1, wherein the smoke evacuation unit has at least one venting element.

4. The magnetic suctioning cannula apparatus of claim 1, wherein the magnetic housing component is positioned on an anterior wall having a substantially planar surface.

5. The magnetic suctioning cannula apparatus of claim 1, wherein the magnetic housing component is securely connected to a hand-held surgical retractor.

6. The magnetic suctioning cannula apparatus of claim 1, wherein the magnetic housing component is securely connected to a self-retaining surgical retractor.

7. A magnetic suctioning cannula system, the system comprising:
   a housing having a first closed end and an opposing end;
   a magnetic component, the magnetic component configured to securely magnetically connect one or more surgical retractors to an anterior surface of the housing;
   a suctioning cannula component, the suctioning cannula having component suction tubing operatively connected to the opposing end of the housing via a suction aperture;

a smoke evacuation element, the smoke evacuation element having at least one slotted vent configured to vent surgical smoke and fumes, and at least a portion of the smoke evacuation element being connected to at least one of a first side wall and a second side wall of the housing; and a suction management system operatively connected to the housing first closed end or opposing end via the suction aperture and the at least one slotted vent of the smoke evacuation element.

8. A method of surgical smoke evacuation by a magnetic suctioning cannula apparatus, comprising the steps of:

providing a magnetic suctioning cannula apparatus having a smoke evacuation unit;

providing one or more surgical retractors in an operatively fixed position;

securing the magnetic suctioning cannula apparatus via a magnetic connection to the one or more surgical retractors creating a secured position;

testing the secured position of the magnetic suctioning cannula apparatus secured to the one or more surgical retractors;

testing the secure position of the magnetic suctioning cannula apparatus secured to one or more electrosurgical devices;

further comprising:

connecting the magnetic suctioning cannula apparatus to a suction management system;

testing the secured position of the magnetic suctioning cannula apparatus connected to the suction management system;

monitoring the function of the smoke evacuation unit during performance of a surgical procedure;

concluding the surgical procedure; and disconnecting the magnetic suctioning cannula apparatus.

* * * * *